United States Patent
Pfleger

Patent Number: 5,799,846
Date of Patent: Sep. 1, 1998

[54] HOLDER FOR A CONTAINER WHICH ADMINISTERS A FEEDING PRODUCT TO HUMANS

[76] Inventor: Frederick W. Pfleger, 1152 Barbara Dr., Cherry Hill, N.J. 08003

[21] Appl. No.: 744,974

[22] Filed: Nov. 7, 1996

[51] Int. Cl.[6] ................................................ A45F 5/00
[52] U.S. Cl. ........................... 224/148.7; 244/148.2; 244/265; 244/185; 128/DIG. 6
[58] Field of Search ...................... 224/148.1, 148.2, 224/148.7, 186–190, 197, 200, 251, 259, 261, 262, 263, 265, 185, 268; 128/DIG. 6

[56] References Cited

U.S. PATENT DOCUMENTS

| | | | |
|---|---|---|---|
| 191,782 | 6/1877 | Smith, Sr. | 224/190 |
| 791,855 | 6/1905 | Alexander | 224/200 |
| 1,460,821 | 7/1923 | Morris | 224/187 |
| 2,085,984 | 7/1937 | Kruithof | 224/188 |
| 2,676,207 | 4/1954 | Hunt | 224/262 |
| 2,723,665 | 11/1955 | Goldsmith | 224/148.2 |
| 3,090,621 | 5/1963 | Heimers et al. | 224/200 |
| 3,547,322 | 12/1970 | Dawson et al. | 224/148.2 |
| 4,438,763 | 3/1984 | Zablen | 224/148.2 |
| 5,161,722 | 11/1992 | Hembree | 224/148.7 |
| 5,353,977 | 10/1994 | Schiro, Jr. et al. | 224/188 |
| 5,626,270 | 5/1997 | Tseng | 224/148.2 |

*Primary Examiner*—Henry J. Recla
*Assistant Examiner*—Gregory M. Vidovich

[57] ABSTRACT

A portable holder for holding containers for feeding a product from the container to the human body such as intravenous feeding or colon flushing in which the holder is strapped to the upper torso of the human body. Being strapped to the body, it enables the person to be mobile without having to push along a cart or a stand. It also gives the person an unlimited range since the container goes with the person.

10 Claims, 1 Drawing Sheet

5,799,846

1

HOLDER FOR A CONTAINER WHICH ADMINISTERS A FEEDING PRODUCT TO HUMANS

CROSS REFERENCES TO RELATED APPLICATIONS

There are no cross references to related applications.

BACKGROUND OF THE INVENTION

1. Field of Invention

With more and more medical procedures being transferred from the hospital to the home, it is getting more important to provide the procedures with as little inconvenience as possible, have the product being used as inexpensive as possible and provide the ability to perform the procedure while the person still maintains his mobility.

This invention describes a container holder which holds a container containing a product to be administered to a human being whether it be an intravenous feeding product or a colostomy irrigation product, etc while the human being is mobile, sitting, or lying down.

2. Description of Prior Art

Previous devices for holding a container with a product to be administered to a human being are difficult to assemble to the body, are mounted to the rear of the body, are mounted to a carriage which the person pushes about, are very expensive, and contain many parts needing adjustments.

SUMMARY OF THE INVENTION

This invention describes a holder for administering a product to a human being that is low cost, stable to wear, easy to mount, and collapsible for storage.

Among the objects of the present invention is to provide a container holder that can be easily attached to the body.

It is a more particular object of the present invention that the user has both hands free while in use.

It is a more particular object of the present invention to provide a holder that enables the user to be completely mobile.

It is a more particular object of the present invention to provide a holder that can be used for many different types of procedures.

It is a more particular object of the present invention to provide a holder that is relatively inexpensive.

It is a more particular object of the present invention to provide a holder, that is adjustable to various angular positions to complement the position of the body whether the body is prone, sitting, or standing and the holder is still above the body.

It is a more particular object of the present invention to provide a holder that can be disassembled to reduce its length for ease of storage or for transporting.

Other objects of the present invention will become apparent upon reading the following specifications and referring to the accompanying drawings which form a material part of this disclosure.

This invention accordingly consists of the features of construction, combinations of elements and appearance of parts, which will be exemplified in the construction herein after described, and the scope of which will be indicated by the appended claims.

2

Figure 2:
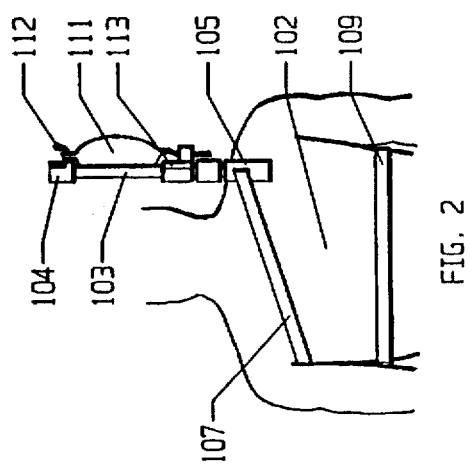

FIG. 2 is a rear view of the body with the holder of the invention shown assembled to the body.

Figure 3:
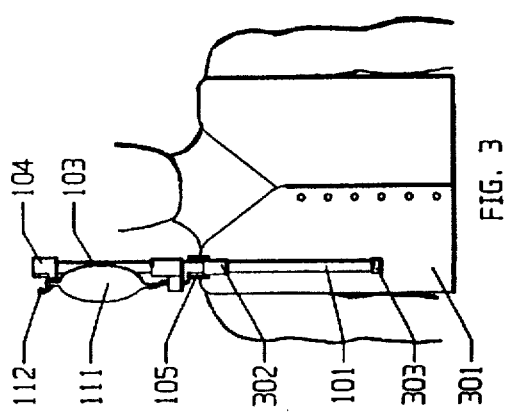

FIG. 3 is a front view of the body with the holder of the invention assembled to the body by use of upper body clothing.

Figure 4:
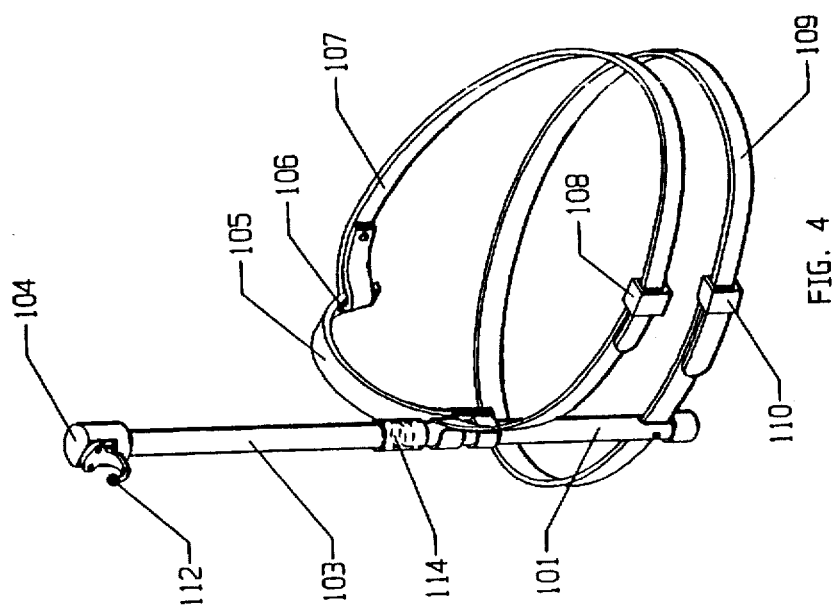

FIG. 4 is a perspective view of the holder with a connector for reducing its length.

Figure 5:
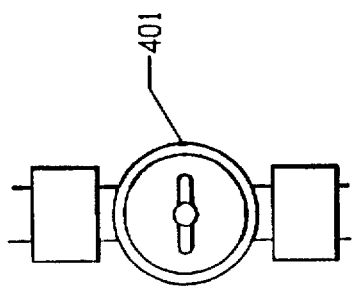

FIG. 5 is a partial view of the rod with a swivel joint attached at its central portion.

DESCRIPTION OF THE PREFERRED EMBODIMENTS

Figure 1:
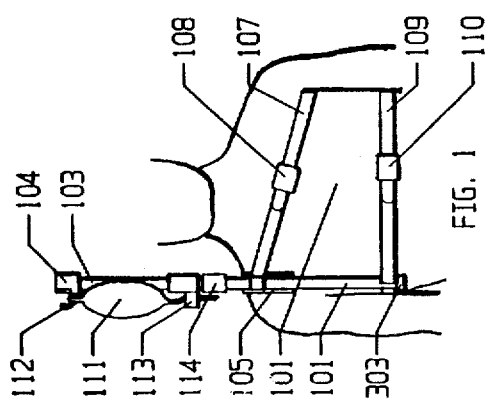
FIG. 1 is a front view of the body with the holder of the invention assembled to the body.

Referring now to FIG. 1, the holder is designated as 101 while the body is designated as 102. The holder 101, comprises an upright rod 103, terminating at its upper end with a container holder 104, in this example a common hook. It is readily understood that a single or a multiplicity of various types of hook or hooks could be used. An ordinary clamp could also be used. From the container holder 104, downward a given distance is a shoulder holder 105, which is secured to the upright rod 103. The shape of the shoulder holder approximates what is required to fit comfortably on the shoulder of the body. At the outer end of the shoulder holder 105, is an opening 106, FIG. 2 & 4, through which a strap 107, is secured. This strap 107 encompasses the body by passing from the shoulder holder 105, around the back to the underarm of the opposite side of the body 102. It then passes the front of the body through a yielding member or an adjusting member 108. This yielding or adjusting member 108, can be an elastic member or a buckle. For ease of assembling this shoulder holder 105 to the body, the shoulder holder 105 is placed on the shoulder of the body 102, while the belt 107 is put over the head and under the other arm than the one with the shoulder holder 105. The belt 107 is then tightened by the relaxing of the elastic member or the drawing up of the belt 107 into the buckle 108.

At the lower end of rod 103, is a second belt 109, secured to the lower end by a loop around the outside of rod 103, or an obstruction fastened to the belt 109, while it passes through openings in the rod 103. The end of the belt 109, extending to the front of the body can have Velcro (a pressure sensitive adhering element comprising hook and loop fasteners) or a buckle 110 attached to it. After assembling the belt 109 to the lower portion of the chest of body 102, it may then be necessary to readjust the fit of the belt 107. This can be accomplished by use of the elastic material or adjusting the buckle 108.

With the holder securely positioned on the body 102, a bag or any other type of container 111, can be hung from the container holder 104. As shown in this application, the hanging of the container 111, is achieved by using a hook 112, fastened to container holder 104.

As a result holder 101 when secured to body 102, can be used with intravenous feeding of medicine or colostomy irrigation, etc. Since the holder is not mounted to the floor or wall hangers, the body can move about freely.

In some intravenous feed systems, the intravenous medicine is fed to the body by means of a pump. In order to accomplish this, the pump 113 can also be secured to the upright arm 103, as shown.

In certain applications, it may be desirable to make holder 101 more portable for storage or packing. To achieve this, the upper end of rod 103 can be made detachable from the lower end of rod 103. A coupling 114 can be used to connect the two parts while in use. Another method to make the holder 101 more portable would be to make the upper end of rod 103 telescoping with the lower end of rod 103. Any of the well known telescoping means would be applicable.

If the person is to use this apparatus over a long period of time such as when there is a chronic ailment, it may be desirable to substitute for the adjusting straps 107 and 109, an upper body garment such as a vest as shown in FIG. 3, since vests can be made to securely fit the body. The vest 301, FIG. 3, is provided with a top holder 302 secured to the upper portion of the vest 301. To the lower portion of vest 301 is secured a lower holder 303 to receive the lower end of rod 103. The top holder 302 is located just below the shoulder holder 105. Top holder 302 and the lower holder 303, are located to secure the rod 103 in correct alignment with the body. In using the vest 301 to hold the apparatus, the user only has to remove the vest 301 with the holder 101, and reinstall the vest 301 for the next use of the apparatus.

In certain applications it may be desirable to have a holder that is capable of being assembled to the body 102 for sitting, standing or moving about while still functioning while the body 102 is prone such as lying in bed. To accomplish this, the locking swivel joint 401 can be substituted for the coupling 114. As a result, the rod 103 can be positioned at any position from straight to 90 degrees of rotation. In any case the container 111 is always above the body 102.

What has been described then is a holder for feeding a product from a container to the body that can be assembled to the body, adjusted to fit securely so that the holder can be used with the patient sitting, standing, moving about, and prone on a bed.

What is claimed is:

1. A holder for holding a container, said holder adapted to be secured to the body of a human being and to hold the container which contains a feeding product for the human being, said holder comprising, a rod having a lower end at one end and an attachment end at the other end, an attachment member at the attachment end for holding the container, a shoulder holder configured to be supported on one shoulder of the human being having a free end and a fastening end wherein said fastening end is fastened between said lower end and said attachment end of said rod, a first belt securing means comprising a first belt having a first end attached to said free end of said shoulder holder, an intermediate section which runs across the back of said human being and under the armpit opposite the one shoulder and across the chest of the human being and a second end which attaches to said rod at the approximate position of said fastening end of said shoulder holder, a second belt securing means comprising a second belt having a first end and a second end attached to the lower end of said rod, such that securing said first belt securing means and said second belt securing means to the human being provides a means for holding the container to allow the feeding of a product to be administered to the human being.

2. A holder according to claim 1 wherein said first belt securing means includes an elastic material, such that said first belt securing means adjusts said holder to various sizes of human beings.

3. A holder according to claim 1 wherein said second end of said first belt is attached to sid rod by a first belt adjusting means secured to said rod at the approximate position of fastening end, wherein said second end of said first belt is attached to said rod by said shoulder holder and adaptable to secure said second end of said first belt to adjustably said rod.

4. A holder according to claim 3 wherein said second belt includes, a second belt tightening means located between said first end and said second end of said second belt.

5. A holder according to claim 3 wherein said first belt tightening means includes a belt buckle.

6. A holder according to claim 4 wherein said second belt tightening means further includes a belt buckle.

7. A holder for holding a container, said holder adapted to be secured to the body of a human being and to hold a container which contains a product to be administered to the human being, said holder comprising, a rod having a lower end at one end and an attachment end at the other end, an attachment member at the attachment said lower end of said rod having at least one opening therethrough end for holding the container, a shoulder holder configured to be supported on one shoulder of the human body, having one end attached to said rod and a free end, a first strap having one end secured to said rod near the one end of the shoulder holder and a free end extending partially across the chest of the human being, a second strap having one end secured to the free end of the shoulder holder and a free end extending under the opposite shoulder and across the chest of the human being toward said free end of said first strap, a first attaching means for attaching said free end of said first strap and said free end of said second strap, a third strap having first and second ends, said third strap passing through said at least one opening such that said third strap is secured to said rod, a second attaching means for attaching said first and second ends of said third strap, such that securely attaching the free end of the first strap to the free end of the second strap and the first and second ends of the third strap secures the rod and the container holder to the human being to allow the product in the container holder to be administered to the human being.

8. A holder for holding a container according to claim 7 wherein said rod is divided into an upper half portion and a lower half portion including a connector for holding said upper half portion and said lower half portion together.

9. A holder for holding a container according to claim 7 wherein said first attaching means and said second attaching means are adjustable.

10. A holder for holding a container according to claim 8 wherein said connector is a swivel joint used when attached to the human being whether the human being is in any angular position from erect position to a position of lying down.

* * * * *